US00PP33436P2

(12) United States Plant Patent
van Kesteren

(10) Patent No.: US PP33,436 P2
(45) Date of Patent: Aug. 31, 2021

(54) ***DELPHINIUM* PLANT NAMED 'COADELCHMO'**

(50) Latin Name: ***Delphinium* hybrid**
Varietal Denomination: COADELCHMO

(71) Applicant: Anthony Paul Coakley, Glasgow (GB)

(72) Inventor: Marc van Kesteren, Noordwijkerhout (NL)

(73) Assignee: Anthony Paul Coakley, Glasgow (GB)

( * ) Notice: Subject to any disclaimer, the term of this patent is extended or adjusted under 35 U.S.C. 154(b) by 0 days.

(21) Appl. No.: 17/077,627

(22) Filed: Oct. 22, 2020

(51) Int. Cl.
*A01H 5/02* (2018.01)
*A01H 6/72* (2018.01)

(52) U.S. Cl.
USPC ..... Plt./423
CPC ..... *A01H 6/72* (2018.05)

(58) Field of Classification Search
USPC ..... Plt./423
CPC ..... A01H 6/72; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Delphinium* hybrid plant named 'COADELCHMO' which is characterized by basal foliage and a compound terminal raceme held within and above the foliage, flowers loosely held on long pedicels, flowers with an abundance of tepaloids, a unique color appearance of the perianth comprised of a large light yellow-green center, becoming progressively suffused with violet towards the outer whorls, with a light blue at the outer tepal whorl, and the stability and uniformity of these traits through successive cycles of asexual propagation.

3 Drawing Sheets

Latin name of the genus and species: The Latin name of the genus and species of the novel variety disclosed herein is *Delphinium* hybrid.

Variety denomination: The inventive variety of *Delphinium* disclosed herein has been given the variety denomination 'COADELCHMO'.

BACKGROUND OF THE INVENTION

Parentage: The claimed plant originated as a naturally occurring, whole-plant mutation of *Delphinium* hybrid 'Sweet Sensation' (U.S. Plant Pat. No. 20,341). In the summer of 2012 the inventor discovered the mutation at a commercial greenhouse in Noordwijkerhout, Netherlands, growing amongst a crop of *Delphinium* hybrid 'Sweet Sensation'. The mutation was noted for its unique light pink flower color and was subsequently isolated for further evaluation in order to confirm the distinctness and stability of the characteristics first observed.

Asexual Reproduction: In the spring of 2015, 'COADELCHMO' was first asexually reproduced in Glasgow, Scotland by way of softwood stem cuttings. The claimed plant was found to asexually reproduce in uniform and stable manner and four successive cycles of vegetative propagation have proven to be true to type.

SUMMARY OF THE INVENTION

The following characteristics have been repeatedly observed and represent the distinguishing characteristics of the new *Delphinium* plant, 'COADELCHMO'. These traits, in combination, distinguish 'COADELCHMO' as a new and distinct cultivar.

1. 'COADELCHMO' exhibits basal foliage with a compound terminal raceme held within and above the foliage; and 2. 'COADELCHMO' exhibits flowers loosely held on long pedicels along the raceme; and
3. 'COADELCHMO' exhibits flowers with an abundance of tepaloids; and
4. 'COADELCHMO' exhibits flowers with multiple whorls of tightly held tepaloids at the center of the perianth, somewhat more relaxed tepaloids towards the outer whorls of the perianth, and an outer whorl of loosely held tepals; and
5. 'COADELCHMO' exhibits a unique color appearance of the perianth comprised of a large light yellow-green center, becoming progressively suffused with violet towards the outer whorls, with a light blue at the outer tepal whorl.

BOTANICAL DESCRIPTION OF THE PLANT

Figure 1:
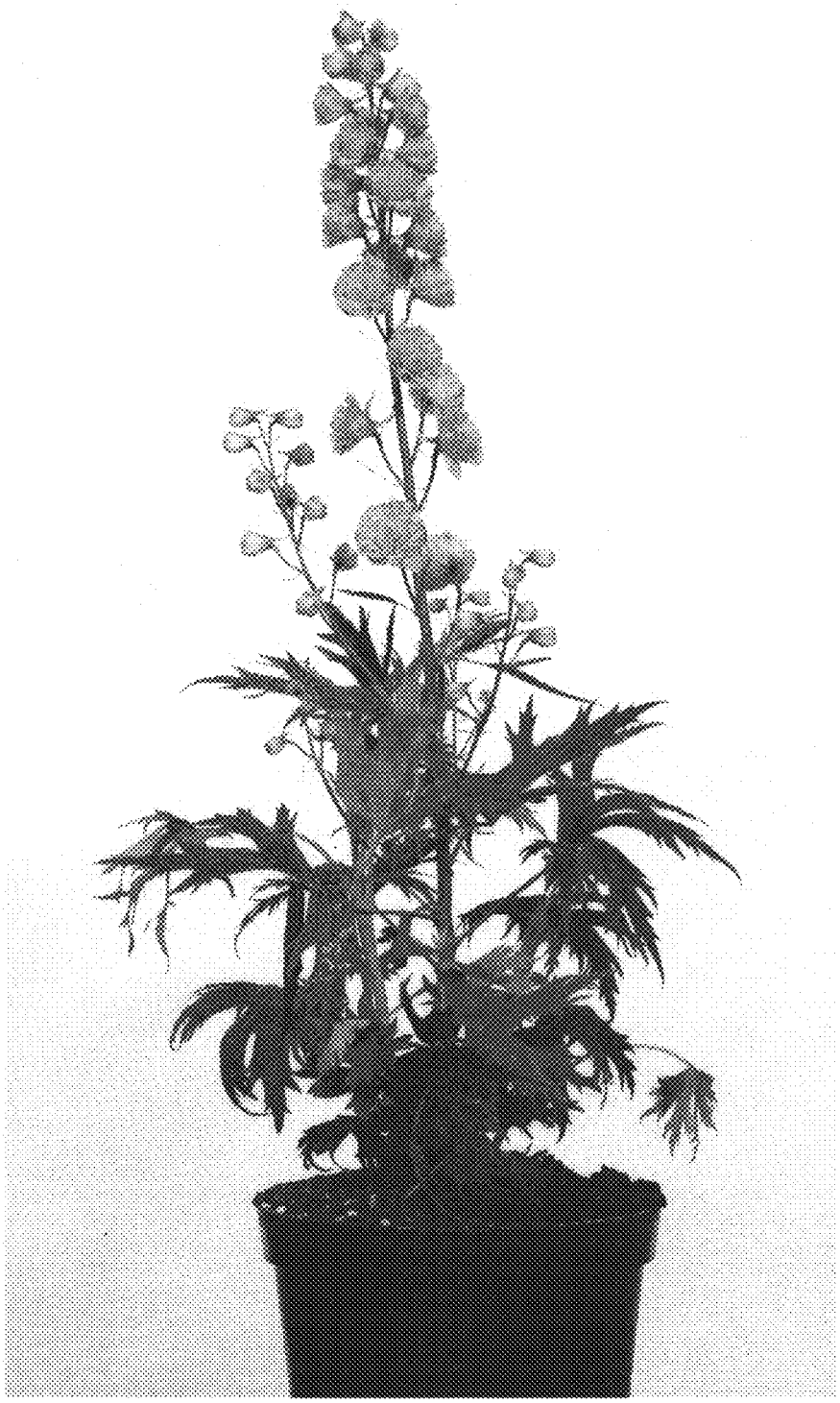
FIG. 1 illustrates, as nearly true as it is reasonably possible to make the same in color photographs of this type, an exemplary 'COADELCHMO' plant at approximately 6 months of age grown in Glasgow, Scotland.
Figure 2:
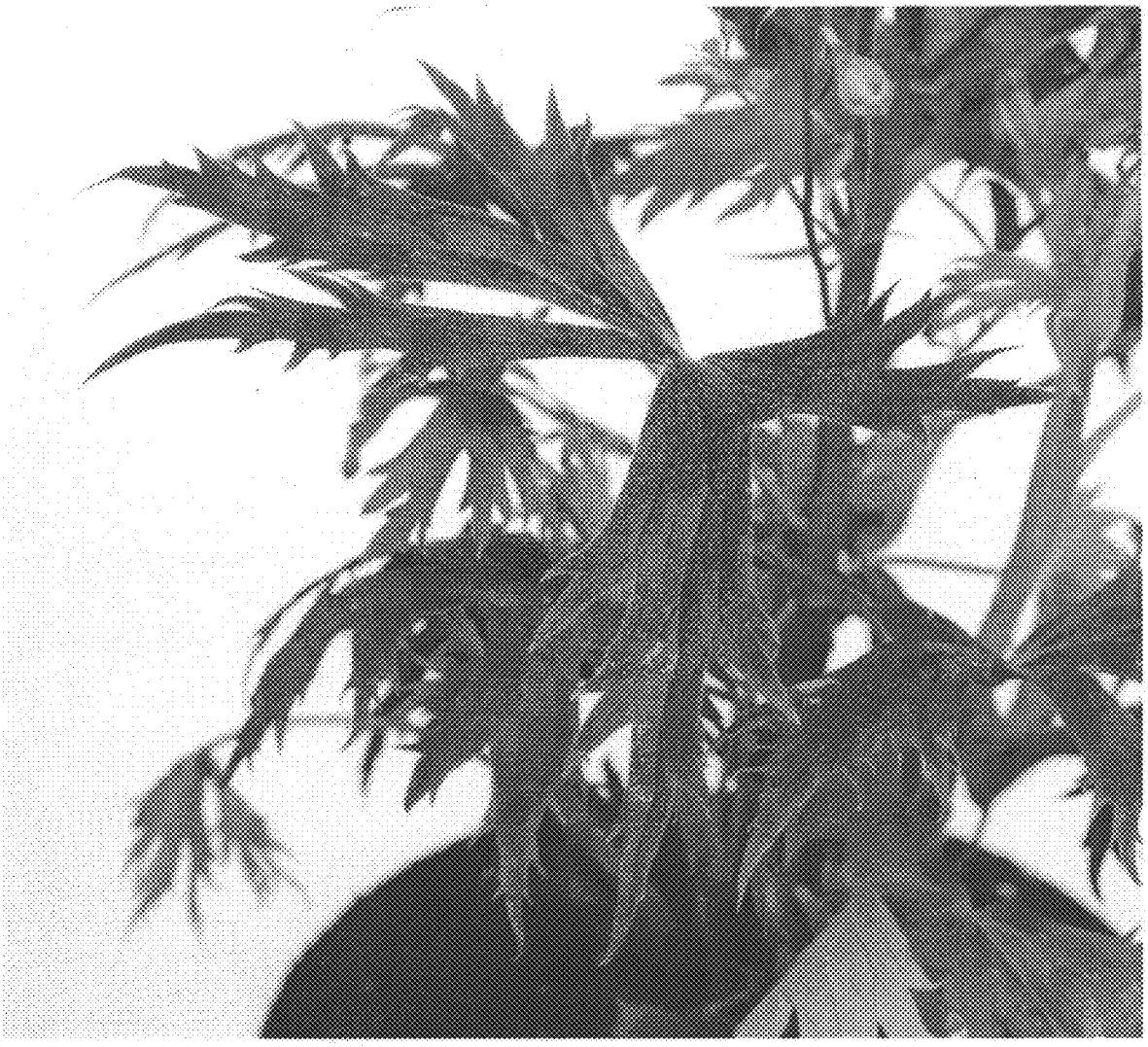
FIG. 2 illustrates, as nearly true as it is reasonably possible to make the same in color photographs of this type, the foliage of 'COADELCHMO'.
Figure 3:
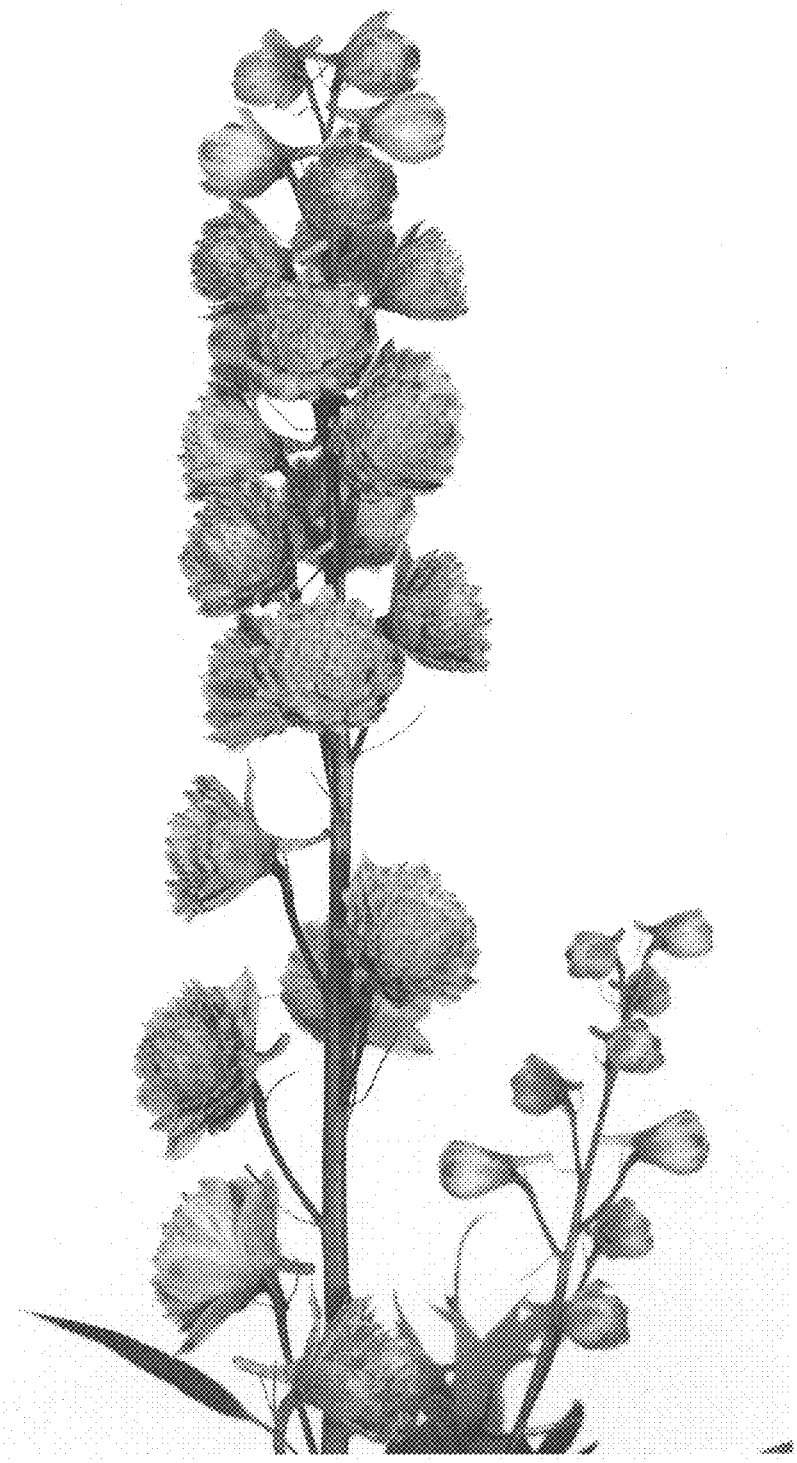
FIG. 3 illustrates, as nearly true as it is reasonably possible to make the same in color photographs of this type, the flowers of 'COADELCHMO'.

The following is a detailed botanical description of a new and distinct *Delphinium* plant known as 'COADELCHMO'. Plant observations were made on a 6 month-old plant growing in Glasgow, Scotland. The observed plant was field-grown in full exposure to natural sunlight, maintained with organic fertilizer and overhead irrigation. Chemical control of powdery mildew was utilized in production but no other pest or pathogen countermeasures were employed. For the purposes of these observations, the observed plant was harvested from the field and potted into a 19 cm nursery container. Observation data was recorded in July of 2020.

Those skilled in the art will appreciate that certain characteristics will vary with older or, conversely, younger plants. 'COADELCHMO' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, Sixth Edition except where common terms of color are used.

A botanical description of 'COADELCHMO' and comparisons with the parent and most similar commercial cultivar are provided below.

General plant description:

*Plant habit*.—Perennial plant with basal foliage and branched flowering stems, bearing flowers arranged on terminal racemes held within and above the foliage.

*Plant profile*.—Narrow ovate to ovate.

*Height*.—34.0 cm to the top of the foliar plane; 60.5 cm to the top of the floral plane.

*Spread*.—34.0 cm.

*Plant vigor*.—Moderately vigorous.

*Growth rate*.—Moderately fast growing.

*Propagation*.—Method — Softwood stem cuttings. Time to initiate rooting — 6 weeks at an average ambient temperature of 15 degrees Celsius. Time to produce flowering plant from rooted cutting — Approximately 6 months in an 11 cm container.

*Pest resistance and susceptibility*.—Not any more or less susceptible to pests or diseases known to effect *Delphinium* sp.

*Environmental tolerances*.—Adapt to, at least, USDA Zones 5 to 9 and temperatures ranging from minus 23 degrees Celsius to 35 degrees Celsius; moderate tolerance to rain; low tolerance to wind.

Root system:

*Description*.—A moderately dense network of relatively shallow thin, fibrous feeder roots and deeper thick anchor roots.

Stems:

*Branching habit*.—No vegetative branches are present, however branched flowering stems are present.

*Flowering stem*.—Quantity — Three. Attitude — Erect; near vertical. Aspect — Generally rounded; slightly angular. Strength — Strong. Length — 14.6 cm. Diameter — 0.7 cm. Internode length — 1.65 cm. Texture — Young stems are densely pubescent; hairs are 0.1 cm on average and are colored a translucent white, nearest to RHS NN155D. Mature stems are glabrous. Luster — Matte, due to the presence of epicuticular wax. Color, developing stems — Yellow-green, nearest to RHS 144B. Color, mature stems — Yellow-green, nearest to a combination of RHS 146A and 146B, and covered with an epicuticular wax which is colored nearest to in between green and greyed-green, RHS 138B and 191A. Color at the internodes — Yellow-green, nearest to a combination of RHS 146A and 146B, and covered with an epicuticular wax which is colored nearest to in between green and greyed-green, RHS 138B and 191A.

Foliage:

*Arrangement*.—Alternate.

*Attachment*.—Petiolate.

*Division*.—Simple.

*Quantity*.—11 stem leaves.

*Shape*.—Palmate with a reniform outline; deeply lobed to near cleft.

*Lobes*.—Depth of sinuses — Deep. Sinus orientation — Divergent.

*Aspect*.—Flat and reflexed.

*Attitude*.—Outward.

*Length*.—12.7 cm.

*Width*.—17.8 cm.

*Apex*.—Narrowly acute.

*Base*.—Truncate to hastate; lobes free.

*Margins*.—Coarsely serrate; moderately to densely pubescent with very short, soft hairs with an average length of 0.05 cm and colored white, nearest to RHS NN155D.

*Texture and pubescence, adaxial surface*.—Smooth; main veins and secondary veins are sparsely covered with very short, soft hairs with an average length of 0.05 cm and colored white, nearest to RHS NN155D.

*Texture and pubescence, abaxial surface*.—Smooth; moderately to densely pubescent with very short, soft hairs with an average length of 0.05 cm and colored white, nearest to RHS NN155D.

*Luster, adaxial surface*.—Slightly glossy.

*Luster, abaxial surface*.—Matte.

*Color*.—Juvenile foliage color, adaxial surface — Yellow-green, nearest to RHS 144A. Juvenile foliage color, abaxial surface — Yellow-green, nearest to in between RHS 144A and 146B. Mature leaf color, adaxial surface — Nearest to in between green and yellow-green, RHS NN137A and 144A. Mature leaf color, abaxial surface — Yellow-green, nearest to RHS 147B.

*Venation*.—Type — Laciniate. Vein color, adaxial surface — Yellow-green, nearest to RHS 144A. Vein color, abaxial surface — Yellow-green, nearest to RHS 146B.

*Petiole*.—Length — 8.1 cm. Diameter — Petioles are flattened; 0.35 cm tall and 0.3 cm wide. Strength — Very strong. Texture, adaxial and abaxial surfaces — Smooth and very sparsely covered with very short, soft hairs with an average length of 0.015 cm and colored white, nearest to RHS NN155D. Luster, adaxial and abaxial surfaces — Moderately glossy. Color, adaxial surface — Yellow-green, nearest to in between RHS 144A and 146A. Color, abaxial surface — Yellow-green, nearest to RHS 146A.

*Stipules*.—Absent.

Inflorescence:

*Inflorescence type*.—Compound terminal raceme with a central, main raceme and multiple lateral racemes.

*Natural flowering season*.—Late summer in Glasgow, Scotland.

*Time to flower or response time*.—Approximately 10 months.

*Height*.—The entire compound raceme is 52.4 cm high, from the lowest branching of the peduncle to the apex of the inflorescence. The main, central raceme is 38.3 cm tall.

*Diameter*.—The entire compound raceme is 16.6 cm in diameter; the main, central raceme is 9.6 cm in diameter.

*Quantity of flowers per inflorescence*.—64 on the entire compound raceme; 33 on the main raceme.

*Peduncle*.—Length — Approximately 36.4 cm. Diameter — Approximately 0.5 cm. Attitude — Erect, in an average angle of 0 degrees to the main stem. Strength — Strong. Texture — Smooth and glabrous. Luster — Slightly glossy. Color — Yellow-green, nearest to RHS 146A.

*Bracts*.—Quantity — Two bracts are present at the base of each individual flower. Shape — Linear. Length — 1.3 cm, on average. Width — 0.1 cm, on average. Apex — Narrowly acute. Base — Cuneate. Margin — Entire. Texture — Smooth and moderately covered with short, soft hairs with an average length of 0.1 mm and colored white, nearest to RHS NN155D. Color, adaxial and abaxial surfaces — Yellow-green, nearest to RHS 146B.

Flower bud:

*Shape*.—Broad obovate.

*Length*.—Average of 2.0 cm.

*Diameter*.—1.2 cm tall and 1.2 cm wide.

*Texture*.—Smooth and moderately pubescent; soft white hairs are approximately 0.08 cm long and colored a translucent white, nearest to RHS NN155D.

*Luster*.—Very slightly glossy.

*Color*.—Yellow-green, nearest to RHS 145B, and darker towards the apex, nearest to RHS 144A.

Flower:

*Type and form*.—Rotate; double.

*Aspect*.—Outward.

*Flowering habit*.—Freely flowering.

*Flower longevity on plant*.—Approximately 10 days.

*Longevity of cut flowers*.—Approximately 10 days.

*Persistent or self-cleaning*.—Self-cleaning.

*Fragrance*.—Non-fragrant.

*Diameter*.—Average of 3.9 cm.

*Depth*.—Average of 3.5 cm.

*Perianth*.—No distinct petals and sepals, only tepals and tepaloids are present. Tepals — Quantity — 5 unfused tepals; one dorsal, two lateral, and two lower tepals. Arrangement — Rotate; single whorl. Attitude — Relaxed. Aspect — Moderately concave. Length — Dorsal tepal — 2.3 cm. Lateral tepals — 2.1 cm. Lower tepals — 2.2 cm. Width — Dorsal tepal — 1.4 cm. Lateral tepals — 1.5 cm. Lower tepals — 1.15 cm. Shape — Dorsal tepal is elliptic; lateral tepals are broad obovate; lower tepals are obovate. Apex — Dorsal tepal is acute; lateral and dorsal tepals are obtuse. Base — All tepals are broad cuneate. Margin — All tepals are entire and either not undulated or lightly undulated. Texture, luster and pubescence of the upper surface — All tepals are glabrous, moderately velvety, and matte. Texture, luster and pubescence of the lower surface — All tepals are slightly velvety, slightly glossy and moderately covered with very short attenuate hairs with an average length of 0.15 cm and colored white, nearest to RHS NN155D. Color when opening, upper surface — Dorsal tepal — Greyed-green, nearest to RHS 195D; fading to yellow-green towards the base, nearest RHS 146D; fading to blue-green towards the apex, nearest to a mixture of RHS 122A and 122B. Lateral tepals — Yellow-green, nearest to RHS N148D, and lightly suffused with violet, nearest to RHS 84C; fading to blue towards the margins and apex, nearest to RHS 104C; fading to yellow-green towards the base, nearest to a mixture of RHS 145A and 145B. Lower tepals — Yellow-green, nearest to RHS N148D, and lightly suffused with violet, nearest to RHS 84C; fading to blue towards the margins and apex, nearest to RHS 104C; fading to yellow-green towards the base, nearest to a mixture of RHS 145A and 145B. Color when opening, lower surface — Dorsal tepal — Greyed-green, nearest to a mixture of RHS 197D, 198A and 198B; fading to yellow-green towards the base and apex, nearest to a mixture of RHS 146A and 146B. Lateral tepals — Yellow-green, nearest to RHS N148D, and lightly suffused with violet, nearest to RHS 84C; fading to blue towards the margins and apex, nearest to a mixture of RHS 100B and 100C; fading to yellow-green towards the base, nearest to a mixture of RHS 145A and 145B. Lower tepals — Yellow-green, nearest to RHS N148D, and lightly suffused with violet, nearest to RHS 84C; fading to blue towards the margins and apex, nearest to a mixture of RHS 100B and 100C; fading to yellow-green towards the base, nearest to a mixture of RHS 145A and 145B. Color when fully opened, upper surface — Dorsal tepal — Greyed-green, nearest to in between RHS 197D and 198D; fading to yellow-green towards the base, nearest to a mixture of RHS 145A and 145B; fading to violet-blue towards the apex, nearest to RHS 98B; distally margined violet-blue, nearest to RHS 98D. Tepals do not fade with age. Lateral tepals — Yellow-green, nearest to RHS 148D, with a green central blotch, nearest to RHS 133B; fading yellow-green towards the base, nearest to a mixture of RHS 145B and 145C, distally margined violet-blue, nearest to RHS 98C. Tepals do not fade with age. Lower tepals — Yellow-green, nearest to RHS 148D, with a green central blotch, nearest to RHS 133B; fading yellow-green towards the base, nearest to a mixture of RHS 145B and 145C, distally margined violet-blue, nearest to RHS 98C. Tepals do not fade with age. Color when fully opened, lower surface — Dorsal tepal — Greyed-green, nearest to RHS 197D, and suffused blue-green, nearest to RHS 122C; fading to yellow-green towards the base, nearest to RHS 145D; fading to a darker shade of yellow-green towards the apex, nearest to in between RHS 146A and 146B. Tepals do not fade with age. Lateral tepals — Yellow-green, nearest to RHS 145B, with a darker central blotch, nearest to a mixture of RHS 146A and 146B; distally margined violet-blue, nearest to RHS 98C. Tepals do not fade with age. Lower tepals — Yellow-green, nearest to RHS 145B, with a darker central blotch, nearest to a mixture of RHS 146A and 146B; distally margined violet-blue, nearest to RHS 98C. Tepals do not fade with age. Tepal venation color — Fully opened, upper surface — Yellow-green, nearest to RHS 148A. Fully opened, lower surface — Yellow-green, nearest to RHS 148A. Tepaloids — Arrangement — Rotate; the unfused tepaloids are relatively tightly-held in 7 whorls. Attitude — Erect. Aspect — Strongly concave. Quantity — 45. Length — 1.8 cm. Width — 0.8 cm. Shape — Obovate to narrow obovate. Apex — Laciniate, with acute lobe apices. Base — Cuneate. Margin — Entire; slightly undulated. Texture, luster and pubescence of the inner surface — Moderately velvety, glabrous and very slightly glossy. Texture, luster and pubescence of the outer surface — Slightly velvety, glabrous and slightly glossy. Color when opening, upper surface — Outer tepaloids are yellow-green, nearest to RHS 145D, and fading darker towards the base, nearest to RHS 145C; apex is strongly suffused with violet-blue, nearest to RHS 98C. Inner tepaloids are yellow-green, nearest to RHS 145C, and becoming darker towards the apex, nearest to RHS 145B. Color when opening, lower surface — Outer tepaloids are yellow-green, nearest to RHS 145D, with a darker central blotch, nearest to RHS 145C; apices of outer tepaloids are suffused with violet-blue, nearest to RHS 98D. Inner tepaloids are yellow-green, nearest to RHS 145C, and becoming darker towards the apex, nearest to RHS 145B. Color when fully opened, upper surface — Outer tepaloids are violet, nearest to RHS 84C, with a yellow-green central band, nearest to RHS 145C; a green central blotch is present, nearest to RHS 133C; distally margined violet-blue, nearest to RHS 98C. Inner tepaloids are yellow-green, nearest to RHS 145C, and becoming slightly darker towards the apex, nearest to RHS 145B; inner tepaloids are distally margined violet-blue, nearest to RHS 76C. Tepaloids do not fade with age. Color when fully opened, lower surface — Outer tepaloids are violet, nearest to RHS 84C, with a yellow-green central band, nearest to RHS 145C; a green central blotch is present, nearest to RHS 133C; distally margined violet-blue, nearest to RHS 98C. Inner tepaloids are yellow-green, nearest to RHS 145C, and becoming slightly darker towards the apex, nearest to RHS 145B; inner tepaloids are distally margined violet-blue, nearest to RHS 76C. Tepaloids do not fade with age. Tepaloid venation color when fully opened, inner surface — Yellow-green, nearest to RHS 145A. Tepaloid venation color when fully opened, outer surface — Yellow-green, nearest to RHS 145A. Pedicels — Length — 4.9 cm. Diameter — 0.15 cm. Angle — Average angle to peduncle axis is approximately 35 degrees. Strength — Moderately strong to strong. Texture — Smooth and sparsely covered with very short, soft hairs particularly towards the base. Hairs are an average length of 0.1 cm and colored white, nearest to RHS NN155D. Luster — Glossy. Color — Green, nearest to RHS 143A yet darker. Spurs — Quantity — One dorsal tepal spur present. Length — 1.2 cm. Diameter — 0.3 cm. Shape — Oblanceolate. Apex — Obtuse. Base — Broad cuneate. Texture — Moderately rugose and glabrous. Luster — Moderately glossy. Color — Greyed-green, nearest to RHS 197B.

Reproductive organs: All reproductive organs reduced to tepaloids. An undeveloped ovary is present; colored green, nearest to RHS 143A.

Fruit and seed: No fruiting has been observed.

Comparison With the Parent Plant

Plants of the new cultivar 'COADELCHMO' differ from the parent, *Delphinium* hybrid 'Sweet Sensation' (U.S. Plant Pat. No. 20,341) by the characteristics described in Table 1.

TABLE 1

| Characteristic | 'COADELCHMO' | 'Sweet Sensation' |
|---|---|---|
| Plant size. | Smaller than 'Sweet Sensation'. | Larger than 'COADELCHMO'. |
| Abundance of foliage. | Less abundant than 'Sweet Sensation'. | More abundant than 'COADELCHMO'. |
| Inflorescence size. | Larger than 'Sweet Sensation'. | Smaller than 'COADELCHMO'. |
| General appearance of the inflorescence. | Flowers appear to be more loosely held on the raceme due to longer flower pedicels. | Flowers appear to be more tightly held on the raceme due to shorter flower pedicels. |
| Abundance of flowers | More than 'Sweet Sensation'. | Fewer than 'COADELCHMO'. |
| General coloration of the flowers when fully opened. | Exhibits a larger light yellow-green center, becoming progressively suffused with violet towards the outer whorls, with a light blue outer tepal whorl. | Dark purple centers, lightly suffused with light green, becoming purple towards the outer whorls, with dark blue outer whorls. |

Comparison With the Most Similar *Delphinium* Cultivar Known to the Inventor

Plants of the new cultivar 'COADELCHMO' are most similar to the commercial cultivar, *Delphinium* hybrid 'FLOCRYSDEL' (European Community Plant Variety Rights grant number 38904). A comparison of 'COADELCHMO' with *Delphinium* 'FLOCRYSDEL' is described in Table 2.

TABLE 2

| Characteristic | 'COADELCHMO' | 'FLOCRYSDEL' |
|---|---|---|
| Plant size. | Smaller than 'FLOCRYSDEL'. | Larger than 'COADELCHMO'. |
| Length of flowering stem. | Shorter than 'FLOCRYSDEL'. | Longer than 'COADELCHMO'. |
| Inflorescence size. | Smaller than 'FLOCRYSDEL'. | Larger than 'COADELCHMO'. |
| General coloration of the flowers when fully opened. | Exhibits a larger light yellow-green center, becoming progressively suffused with violet towards the outer whorls, with a light blue outer tepal whorl. | Exhibits a smaller light yellow-green center, becoming progressively suffused with violet-blue towards the outer whorls, with a violet-blue outer tepal whorl. |

That which is claimed is:

1. A new and distinct variety of *Delphinium* hybrid plant named 'COADELCHMO', substantially as described and illustrated herein.

* * * * *